(12) United States Patent
Saito et al.

(10) Patent No.: US 7,527,635 B2
(45) Date of Patent: May 5, 2009

(54) SURGICAL KNIFE

(75) Inventors: Tatsuya Saito, Seki (JP); Masahiro Endo, Seki (JP)

(73) Assignee: Kai R&D Center Co., Ltd., Gifu (JP)

( * ) Notice: Subject to any disclaimer, the term of this patent is extended or adjusted under 35 U.S.C. 154(b) by 99 days.

(21) Appl. No.: 10/443,695

(22) Filed: May 21, 2003

(65) Prior Publication Data
US 2003/0225428 A1    Dec. 4, 2003

(30) Foreign Application Priority Data
May 30, 2002    (JP)    ............................. 2002-158153

(51) Int. Cl.
*A61B 17/32*    (2006.01)
(52) U.S. Cl. ...................... 606/167; 606/172
(58) Field of Classification Search ................. 606/167, 606/172; 30/153, 154, 155, 156, 162, 53, 30/55
See application file for complete search history.

(56) References Cited

U.S. PATENT DOCUMENTS

| | | | | | |
|---|---|---|---|---|---|
| 4,835,865 | A | * | 6/1989 | Knoop | 30/162 |
| 5,330,493 | A | * | 7/1994 | Haining | 606/167 |
| 5,481,804 | A | * | 1/1996 | Platts | 30/162 |
| 5,571,127 | A | * | 11/1996 | DeCampli | 606/167 |
| 5,792,162 | A | * | 8/1998 | Jolly et al. | 606/167 |
| 5,909,930 | A | * | 6/1999 | Ragland et al. | 30/125 |
| 5,941,892 | A | * | 8/1999 | Cohn et al. | 606/167 |
| 2002/0124411 | A1 | * | 9/2002 | Huang | 30/161 |

FOREIGN PATENT DOCUMENTS

| | | |
|---|---|---|
| JP | 59-6672 | 2/1984 |
| JP | 61-17717 | 5/1986 |
| JP | 61-17718 | * 5/1986 |
| JP | 06-292677 A | 10/1994 |
| JP | 2608695 | 11/1995 |
| JP | 08-024265 | 1/1996 |
| JP | 2601606 | 1/1997 |

OTHER PUBLICATIONS

Searching PAJ; Patent Abstracts of Japan; Publication No. 08-024265 (English translation of abstract).
Searching PAJ; Patent Abstracts of Japan; Publication No. 07-299076 (English translation of abstract)- Relates to JP 2608695.

* cited by examiner

*Primary Examiner*—Corrine M McDermott
*Assistant Examiner*—Christopher D Prone
(74) *Attorney, Agent, or Firm*—Darby & Darby P.C.

(57) ABSTRACT

In a surgical knife, a slider has an operating part through which the slider is operated. A surface of the operating part is exposed through a window hole of a guide groove and an arresting device for arresting the slider is released by urging the operating part linearly in a direction to be moved. The slider is moved by applying a forward or backward force to the operating part such that a cutter blade of the surgical knife can be moved between its projected position and its withdrawn position with respect to the holder when the holder is held by one hand. Accordingly, a user does not feel pain on his or her finger's when operating the cutter blade.

1 Claim, 12 Drawing Sheets

SURGICAL KNIFE

BACKGROUND OF THE INVENTION

The present invention relates to a surgical knife to be used mainly in medical institutions.

A surgical knife in which a cutter blade is movable between its projected position and its withdrawn position is known in the prior art. For example, in a surgical knife disclosed by JP-B2-2608695, a cutter blade is moved between its projected position and its withdrawn position by rotating an operating part projecting from a surface of a holder and sliding it backward and forward. In a surgical knife disclosed by JP-A-8-24265, a cutter blade is moved between its projected position and its withdrawn position by sliding backward and forward an operating part projecting from an upper surface of a holder.

In the surgical knife disclosed by JP-B2-2608695, since it is necessary for moving the cutter blade between its projected position and its withdrawn position that the operating part is rotated and subsequently is moved backward and forward, the cutter blade cannot be moved by one hand between its projected position and its withdrawn position when the holder is held by the one hand, so that this surgical knife is inconvenient for use by the one hand.

In the surgical knife disclosed by JP-A-8-24265, the operating part projects from the upper surface of the holder. Since the holder is thin, the operating part projecting from the upper surface of the holder is thinner than the holder. Therefore, an upper end of the operating part bites into a thumb so that a user feels a pain when the thumb is pressed against the operating part to move it.

BRIEF SUMMARY OF THE INVENTION

An object of the present invention is to provide a surgical knife in which a cutter blade can be moved by one hand between its projected position and its withdrawn position when a holder is held by the one hand, and a user does not feel a pain on a user's finger when operating the cutter blade.

According to the present invention, in a surgical knife comprising, a holder including a guide groove on a front surface of the holder, a slider movable forward and backward in the guide groove, a cutter blade connected to the slider, and an engaging means for fixing the slider to selected one of a front position of the slider in which front position the cutter blade projects from a front end of the holder and a back position in which back position the cutter blade is contained in the holder, the slider has an operating part through which the slider is operated, a surface of the operating part is exposed through a window hole of the guide groove, the engaging means is capable of being released to make the slider movable by pressing the operating part substantially linearly in one direction to be moved, and the slider is movable in accordance with selected one of forward and backward forces applied to the operating part.

It is preferable in the present invention that the slider has an elastic part and a slider body, the operating part is swingably mounted on the slider body through the elastic part, and the engaging means is capable of being released to make the slider movable by pressing the operating part in a direction from the front surface of the holder toward a reverse surface of the holder to move the operating part in the direction with a deformation of the elastic part.

It is preferable in the present invention that the engaging means has engaging projections formed respectively on upper and bottom surfaces of the operating part and engaging recesses formed respectively on front and back positions of each of upper and lower edges of the window hole of the guide groove so that the slider is fixed by an engagement between the engaging projections and the engaging recesses, and the engaging means is capable of being released to make the slider movable by pressing the operating part in the direction from the front surface of the holder toward the reverse surface of the holder.

It is preferable in the present invention that front and back side surfaces of each of the engaging recesses are perpendicular to a longitudinal direction of the holder, and each of the engaging projections has a trapezoidal shape whose width decreases in the direction from the front surface of the holder toward the reverse surface of the holder.

It is preferable in the present invention that the slider has an elastic part and a slider body, the operating part is mounted on the slider body through the elastic part movably in a transverse direction perpendicular to a longitudinal direction of the holder, and the engaging means is capable of being released to make the slider movable by pressing the operating part in the transverse direction against an elastic force of the elastic part to move the operating part in the transverse direction with a deformation of the elastic part.

It is preferable in the present invention that the slider body and the operating part are separated from each other, the operating part is mounted on the slider body movably in the transverse direction, and the elastic part extends integrally from the slider body in the longitudinal direction to elastically urge the operating part in the transverse direction.

It is preferable in the present invention that the operating part has an engaging projection on a lower surface of the operating part, and the guide groove has engaging holes formed respectively on front and back positions of a bottom surface of the guide groove so that the slider is fixed by an engagement between the engaging projection and selected one of the engaging holes.

It is preferable in the present invention that the slider has a slider body, the operating part has a hinge at an end thereof to be connected to the slider body through the hinge so that the operating part is swingable in a window hole of the guide groove around the hinge, and the operating part has an engaging projection on one of upper and lower surfaces of the operating part so that the engaging projection engages with an engaging portion of the holder to fix the slider in each of a case in which the cutter blade projects from the holder and a case in which the cutter blade is contained in the holder.

It is preferable in the present invention that a part of the operating part extends in the guide groove, and a width of the part of the operating part extending in the guide groove is greater than a width of the window hole.

It is preferable in the present invention that the engaging portion is a recess formed on an inner surface of the guide groove, and the operating part is elastically urged toward the engaging portion so that the engaging projection fits smoothly into the engaging portion.

It is preferable in the present invention that the hinge urges the operating part toward the engaging portion.

It is preferable in the present invention that the slider body has an integrally formed elastic piece to urge the operating part toward the engaging portion.

It is preferable in the present invention that the guide groove has a guide hole extending in the longitudinal direction on a central position of a bottom surface of the guide groove, and the slider has a guide projection to be inserted into the guide hole so that a movable range of the slider is limited.

In a surgical knife comprising, a holder including a guide groove on a front surface of the holder, a slider movable forward and backward in the guide groove, a cutter blade connected to the slider, and an engaging means for fixing the slider to selected one of a front position of the slider in which front position the cutter blade projects from a front end of the holder and a back position in which back position the cutter blade is contained in the holder, according to the invention, the slider has a slider body and a lever-shaped operating part through which the slider is operated, an end of the operating part is connected to the slider body in such a manner that the operating part is swingable around the end of the operating part, the operating part is capable of engaging with a window hole of the guide groove to fix the slider to the holder when the slider is positioned at each of the front and back positions, and the slider is movable when an engagement between the operating part and the window hole is released by swinging the operating part.

It is preferable in the present invention that the guide groove has a recess on each of upper and lower edges of the window hole, the operating part has a projection on each of upper and lower surfaces thereof, and the operating part is swingable by 180 degrees so that the operating part engages with the window hole to fix the slider to the holder with the recess and projection engaging with each other when the slider is positioned at the front position and the operating part engages with the window hole to fix the slider to the holder with the recess and projection engaging with each other when the slider is positioned at the back position.

It is preferable in the present invention that the guide groove has front and back recesses distant from each other in a movable direction of the slider on each of upper and lower edges of the window hole, and the operating part has a projection on each of upper and lower surfaces thereof so that the operating part engages with the window hole to fix the slider to the holder with the front recess and the projection engaging with each other when the slider is positioned at the front position and the operating part engages with the window hole to fix the slider to the holder with the back recess and the projection engaging with each other when the slider is positioned at the back position.

It is preferable in the present invention that a thickness of the operating part is substantially equal to a thickness of an outer peripheral region of the window hole.

According to the present invention, since the surface of the operating part is exposed through the window hole of the guide groove, the engaging means is capable of being released to make the slider movable by pressing the operating part substantially linearly in one direction to be moved, and the slider is movable in accordance with selected one of forward and backward forces applied to the operating part, the cutter blade can be moved by one hand between its projected position and its withdrawn position when the holder is held by the one hand, so that the handling of the surgical knife is easy. Further, since the surface of the operating part is exposed through the window hole of the guide groove, an area of the surface of the operating part can be increased by increasing a width of the window hole, so that a user does not feel a pain on a user's finger when operating the cutter blade with the finger contacting the operating part.

If the slider has the elastic part and the slider body, the operating part is swingably mounted on the slider body through the elastic part, and the engaging means is capable of being released to make the slider movable by pressing the operating part in the direction from the front surface of the holder toward the reverse surface of the holder to move the operating part in the direction with the deformation of the elastic part, and/or if the engaging means has engaging projections formed respectively on the upper and bottom surfaces of the operating part and engaging recesses formed respectively on the front and back positions of each of the upper and lower edges of the window hole of the guide groove so that the slider is fixed by the engagement between the engaging projections and the engaging recesses, and the engaging means is capable of being released to make the slider movable by pressing the operating part in the direction from the front surface of the holder toward the reverse surface of the holder, by increasing the width of the window hole of the guide groove, the user's finger (for example, thumb) can extend into the window hole when pressing the operating part with the user's finger. Therefore, it is not necessary for operating the operating part that the surface of the operating part projects by a great length from the surface of the holder. If the surface of the operating part does not project by the great length from the surface of the holder, the cutter blade is prevented from being moved even when the user, for example, a doctor's smock contacts accidentally the operating part. Further, after being disposed of with the cutter blade being contained by the holder, the operating part is restrained from contacting another member in such a manner that the operating part is operated by the another member to project the cutter blade from the holder.

If the front and back side surfaces of each of the engaging recesses are perpendicular to the longitudinal direction of the holder, and each of the engaging projections has the trapezoidal shape whose width decreases in the direction from the front surface of the holder toward the reverse surface of the holder as shown in FIG. 4, a force pushing and pulling the cutter blade with respect to the holder when the cutter blade is fixed presses the engaging projection into the engaging recess so that the cutter blade is prevented from moving.

If the slider has the elastic part and the slider body, the operating part is mounted on the slider body through the elastic part movably in the transverse direction perpendicular to a longitudinal direction of the holder, and the engaging means is capable of being released to make the slider movable by pressing the operating part in the transverse direction against an elastic force of the elastic part to move the operating part in the transverse direction with the deformation of the elastic part, the operating part can be moved through the surface of the operating part which does not project by the long length from the holder surface and which has an anti-slip texture. Since it is not necessary for moving the operating part that the surface of the operating part projects by the long length from the holder surface, the cutter blade is prevented from being moved even when the user, for example, the doctor's smock contacts accidentally the operating part. Further, after being disposed of with the cutter blade being contained by the holder, the operating part is restrained from contacting another member in such a manner that the operating part is operated by the another member to project the cutter blade from the holder. Even when the surface of the operating part slightly projects from the holder surface, since the operating part is generally urged perpendicular to the holder surface and is not urged in the transverse direction, the operating part is restrained from being moved undesirably.

If the slider body and the operating part are separated from each other, the operating part is mounted on the slider body movably in the transverse direction, and the elastic part extends integrally from the slider body in the longitudinal direction to elastically urge the operating part in the transverse direction, the operating part is linearly moved in the transverse direction so that the user's finger can smoothly move the operating part.

If the operating part has the engaging projection on the lower surface of the operating part, and the guide groove has the engaging holes formed respectively on the front and back positions of the bottom surface of the guide groove so that the slider is fixed by the engagement between the engaging projection and selected one of the engaging holes, the slider can be securely fixed to the holder.

If the slider has the slider body, the operating part has the hinge at the end thereof to be connected to the slider body through the hinge so that the operating part is swingable in the window hole of the guide groove around the hinge, and the operating part has the engaging projection on one of the upper and lower surfaces of the operating part so that the engaging projection engages with the engaging portion of the holder to fix the slider in each of a case in which the cutter blade projects from the holder and a case in which the cutter blade is contained in the holder, the operating part and the slider body are formed in one piece by an injection molding so that a production of them is easy.

If the part of the operating part extends in the guide groove, and the width of the part of the operating part extending in the guide groove is greater than the width of the window hole, the part of the operating part bent at the hinge is prevented from being removed through the window hole.

If the engaging portion is the recess formed on the inner surface of the guide groove, and the operating part is elastically urged toward the engaging portion so that the engaging projection fits smoothly into the engaging portion, the slider can be fixed to the holder automatically for easy handling of the surgical knife.

If the hinge urges the operating part toward the engaging portion, the hinge performs two functions as the hinge and elastic part so that a number of elements of the surgical knife is minimized for easy production thereof.

If the slider body has an integrally formed elastic piece to urge the operating part toward the engaging portion, the elastic urging force for inserting securely the engaging projection into the engaging portion is increased by the elastic piece.

If the guide groove has the guide hole extending in the longitudinal direction on the central position of the bottom surface of the guide groove, and the slider has the guide projection to be inserted into the guide hole so that the movable range of the slider is limited, the slider is prevented from being removed from the holder through a back end of the holder even when the back end of the holder is opened.

According to the present invention, since the slider has the slider body and the lever-shaped operating part through which the slider is operated, the end of the operating part is connected to the slider body in such a manner that the operating part is swingable around the end of the operating part, the operating part is capable of engaging with the window hole of the guide groove to fix the slider to the holder when the slider is positioned at each of the front and back positions, and the slider is movable when the engagement between the operating part and the window hole is released by swinging the operating part, it is necessary for moving the cutter blade that the operating part is pulled out of the window hole, so that the cutter blade is prevented from being moved even when the user, for example, the doctor's smock contacts accidentally the operating part. Further, after being disposed of with the cutter blade being contained by the holder, the operating part is restrained from contacting another member in such a manner that the operating part is operated by the another member to project the cutter blade from the holder.

If the guide groove has the recess on each of the upper and lower edges of the window hole, the operating part has the projection on each of the upper and lower surfaces thereof, and the operating part is swingable by 180 degrees so that the operating part engages with the window hole to fix the slider to the holder with the recess and projection engaging with each other when the slider is positioned at the front position and the operating part engages with the window hole to fix the slider to the holder with the recess and projection engaging with each other when the slider is positioned at the back position, a length of the holder may be short.

If the guide groove has the front and back recesses distant from each other in the movable direction of the slider on each of the upper and lower edges of the window hole, and the operating part has the projection on each of the upper and lower surfaces thereof so that the operating part engages with the window hole to fix the slider to the holder with the front recess and the projection engaging with each other when the slider is positioned at the front position and the operating part engages with the window hole to fix the slider to the holder with the back recess and the projection engaging with each other when the slider is positioned at the back position, it is necessary for moving the cutter blade that the operating part is pulled out of the window hole, so that the cutter blade is prevented from being moved even when the user, for example, the doctor's smock contacts accidentally the operating part. Further, after being disposed of with the cutter blade being contained by the holder, the operating part is restrained from contacting another member in such a manner that the operating part is operated by the another member to project the cutter blade from the holder.

If the thickness of the operating part is substantially equal to the thickness of the outer peripheral region of the window hole, the operating part in the window hole does not project out of the window hole so that the operating part is prevented from being moved undesirably and the cutter blade can be securely kept stationary.

BRIEF DESCRIPTION OF THE SEVERAL
VIEWS OF THE DRAWINGS

DETAILED DESCRIPTION OF THE INVENTION

Figure 1:
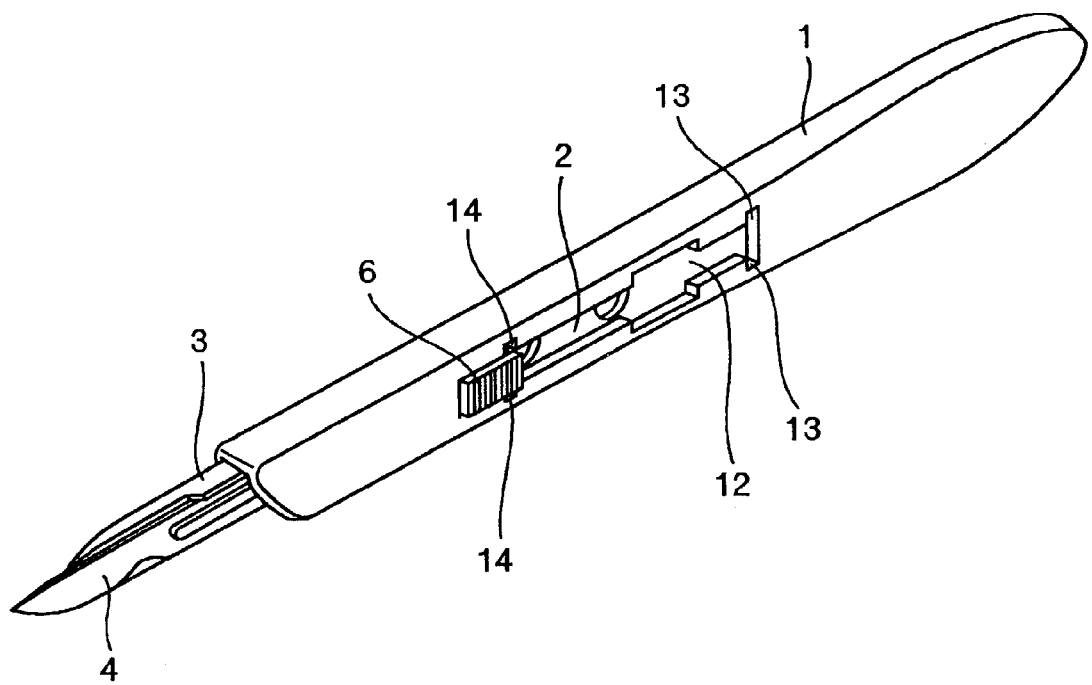
FIG. 1 is a schematic oblique projection view showing a surgical knife of a first embodiment of the invention with a cutter blade positioned at its projected position.
Figure 2:
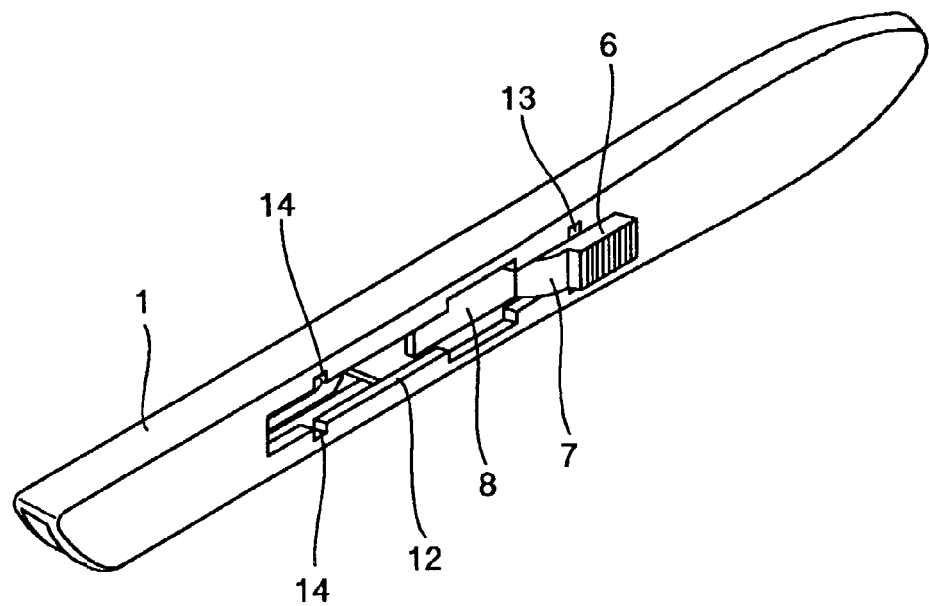
FIG. 2 is a schematic oblique projection view showing the surgical knife of the first embodiment with the cutter blade positioned at its withdrawn position.
Figure 3:
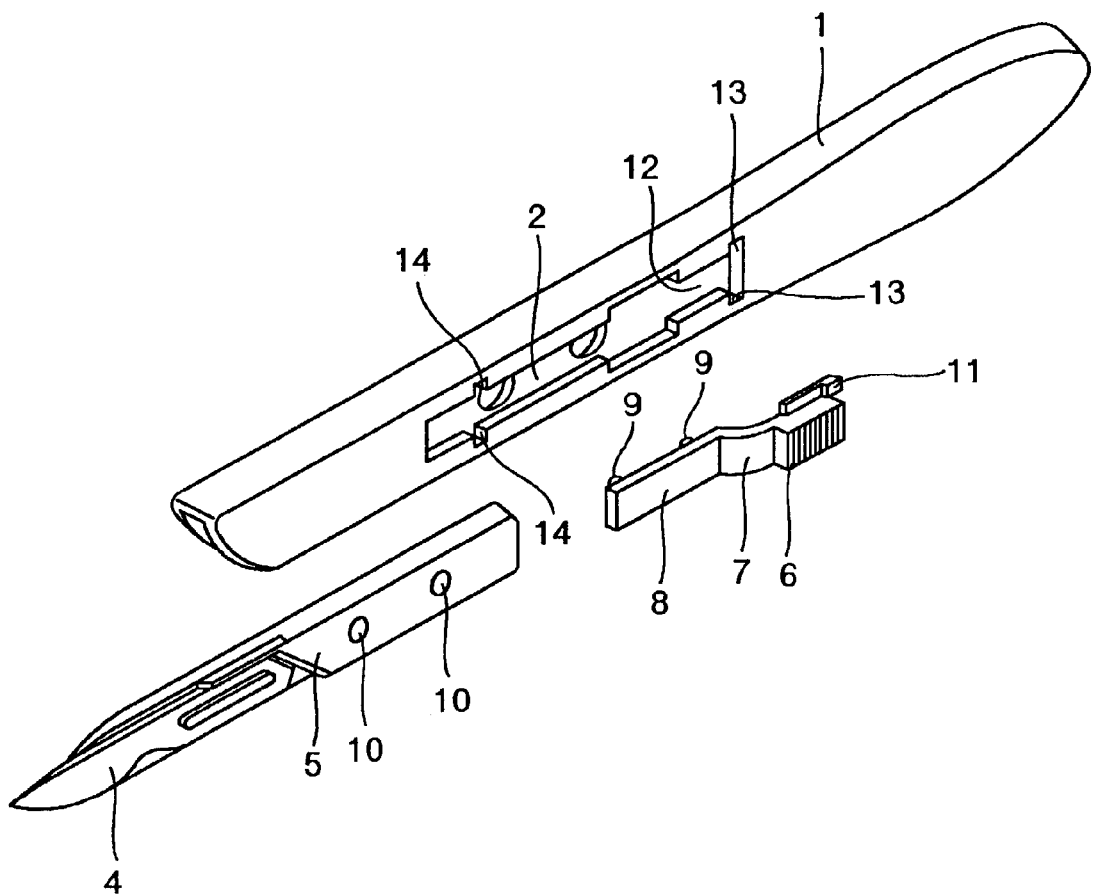
FIG. 3 is a schematic oblique projection exploded view of the surgical knife of the first embodiment.
Figure 4:
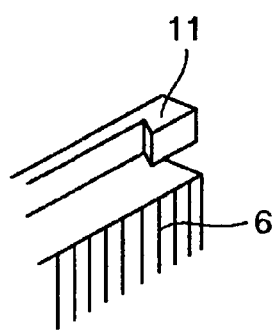
FIG. 4 is a schematic oblique projection enlarged view showing a part of an operating part of the first embodiment.

A first embodiment of surgical knife as shown in FIGS. 1-4 corresponds to the claimed inventions as recited in claims 1-4. A guide groove 2 is formed on a front surface of a holder 1, and a slider 3 is supported in the guide groove 2 to be movable forward and backward. A cutter blade 4 is connected to the slider 3 in such a manner that the cutter blade 4 projects from a front end of the holder 1 when the slider 2 is positioned at its front position, and the cutter blade 4 is completely contained in the holder 1 when the slider 2 is positioned at its backmost position.

Figure 5:
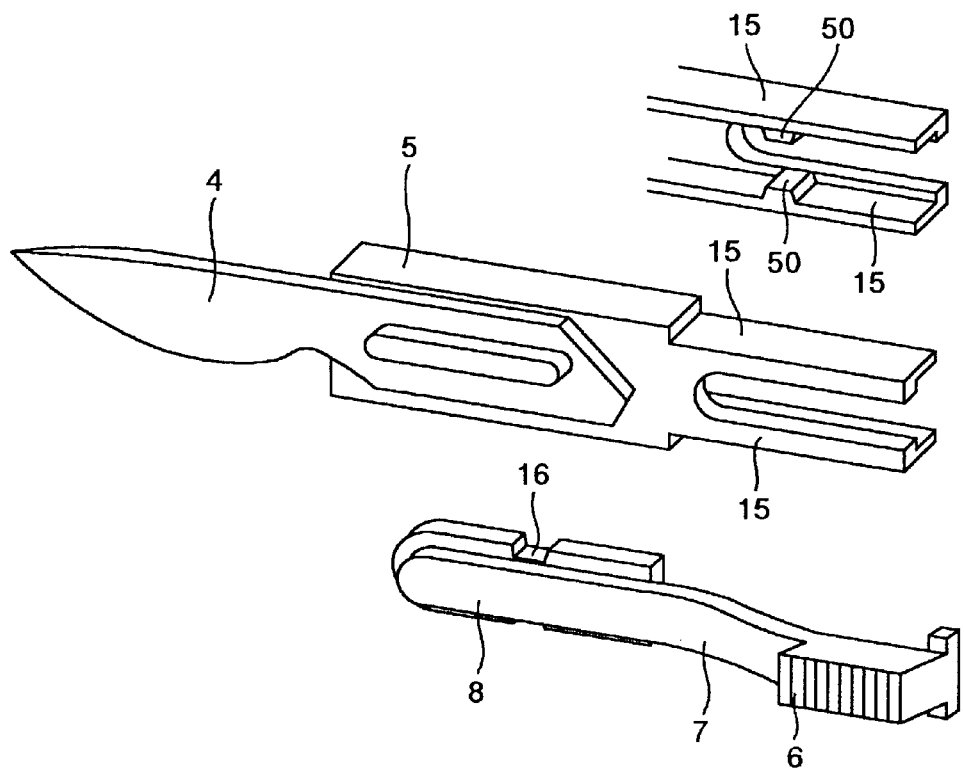
FIG. 5 is a schematic oblique projection view showing another connecting structure between the operating part and a holder body in the first embodiment.
Figure 6:
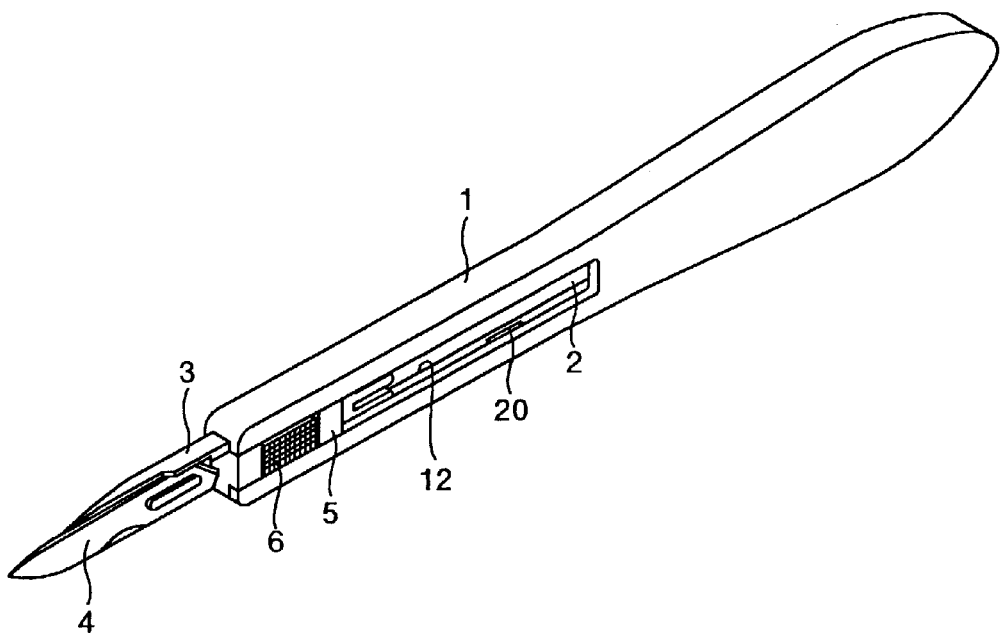
FIG. 6 is a schematic oblique projection view showing a surgical knife of a second embodiment of the invention with a cutter blade positioned at its projected position.
Figure 7:
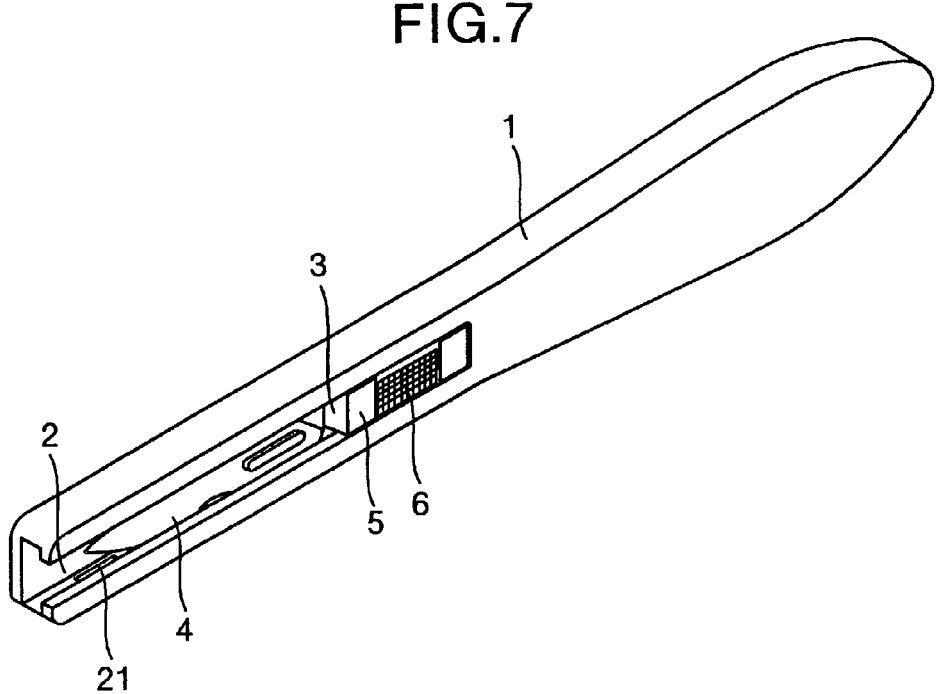
FIG. 7 is a schematic oblique projection view showing the surgical knife of the second embodiment with the cutter blade positioned at its withdrawn position.
Figure 8:
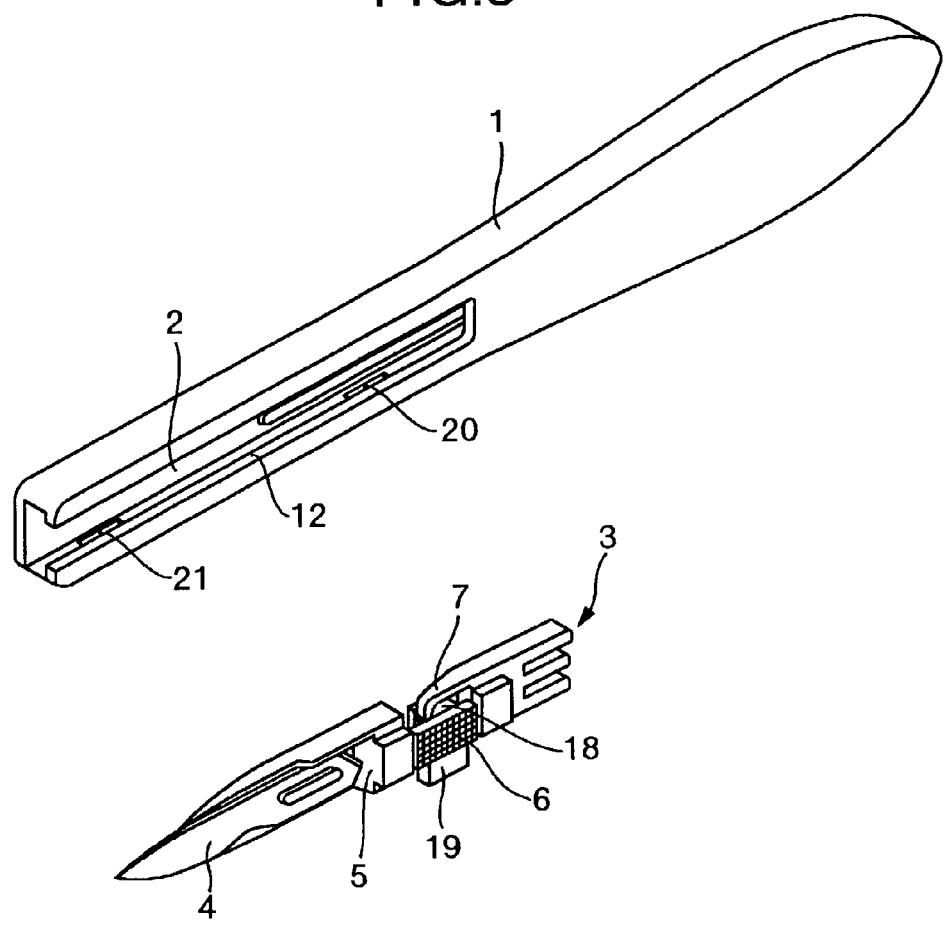
FIG. 8 is a schematic oblique projection exploded view of the surgical knife of the second embodiment.
Figure 9:
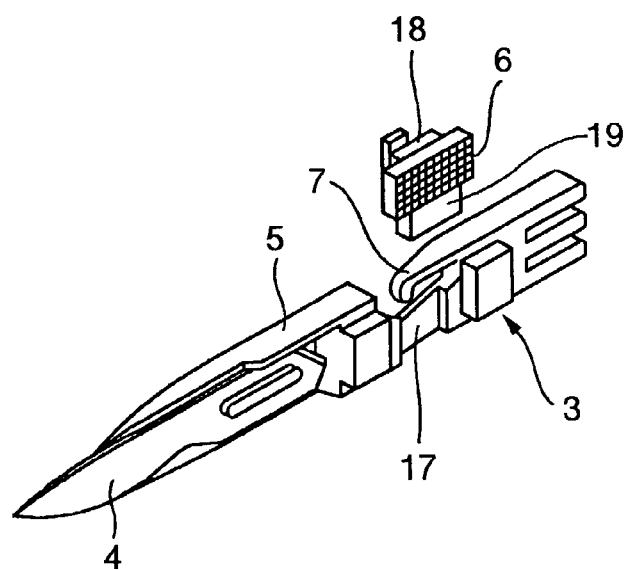
FIG. 9 is a schematic oblique projection view showing a holder of the second embodiment.
Figure 10:
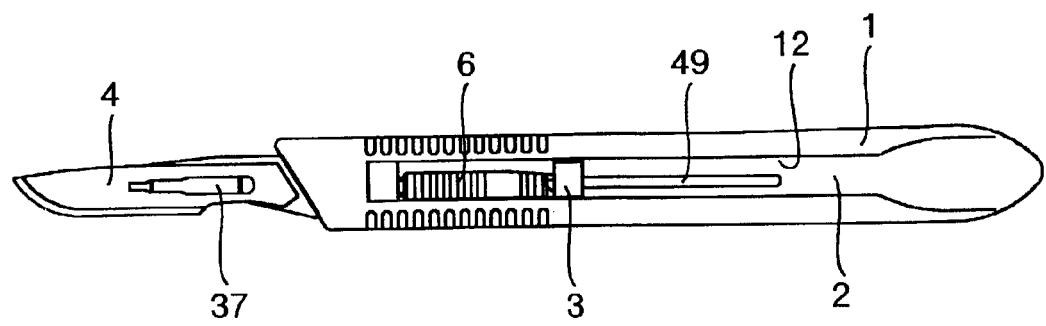
FIG. 10 is a schematic oblique projection view showing a surgical knife of a third embodiment of the invention with a cutter blade positioned at its projected position.
Figure 11:
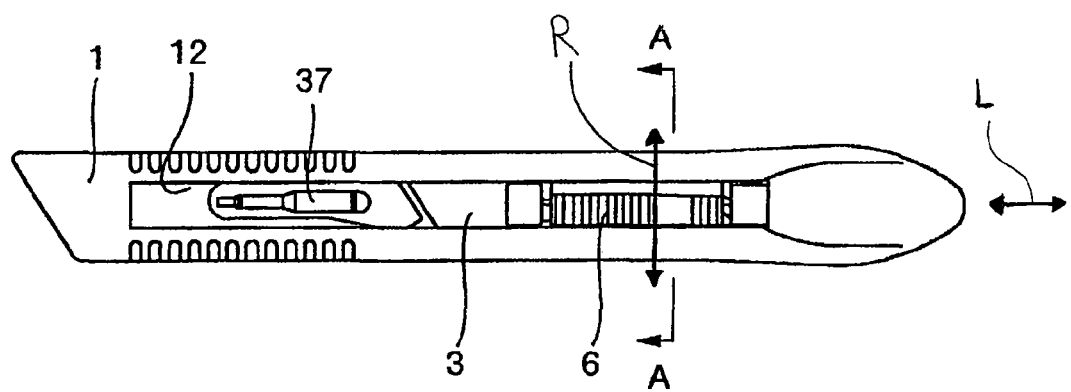
FIG. 11 is a front view of the surgical knife of the third embodiment in which a cutter blade is removed from the surgical knife and a slider is positioned at its withdrawn position.
Figure 12:
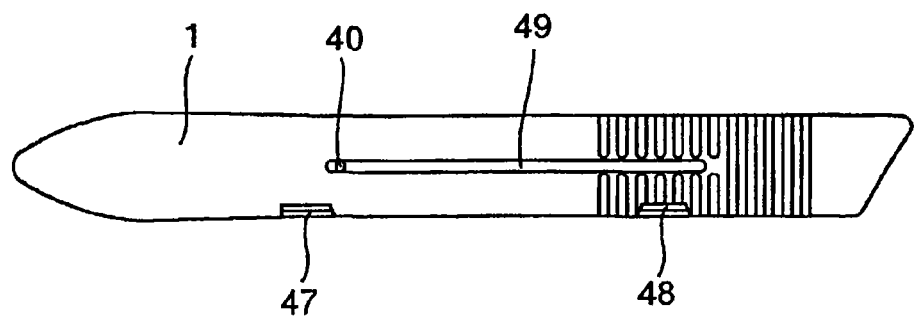
FIG. 12 is a back view of the third embodiment.
Figure 13:
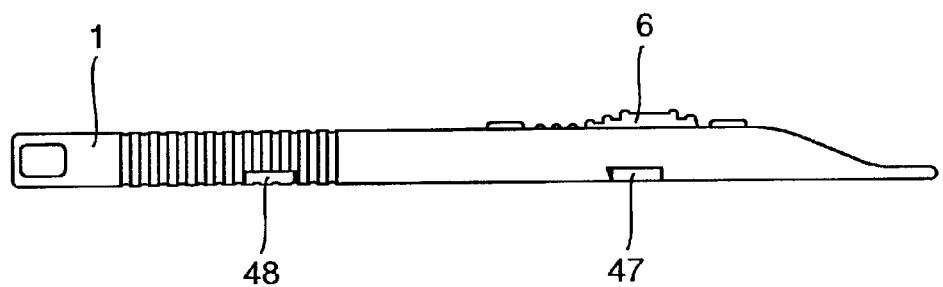
FIG. 13 is a bottom view of the third embodiment.

The slider 3 includes a slider body 5, an operating part 6 and an elastic part 7. The operating part 6 and elastic part 7 are formed in one piece, and a base part 8 formed integrally with the operating part 6 and elastic part 7 is fixed to the slider body 5 so that the operating part 6 is connected to the slider body 5 through the elastic part 7. Since the elastic part 7 extends obliquely with respect to a longitudinal direction of the surgical knife, the operating part 6 is movable in a direction perpendicular to the front surface of the holder 1. The base part 8 includes projections 9 fitted in respective holes of the slider body 5 to be fixed permanently. As shown in FIG. 5, elastic pieces 15 of L-shaped cross-section may extend from a back end of the holder body 5 so that the base part 8 may be received between the elastic pieces 15 while engaging recesses of the base part 8 engage with engaging protrusions 50 of the holder body 5, so that the base part 8 is fixed to the slider body 5.

Upper and lower surfaces of the operating part 6 have engaging projections 11 facing to the front surface of the holder 1. The engaging projections 11 have respective trapezoidal shapes each of which has a width decreasing in a direction from the front surface of the holder 1 toward a reverse surface of the holder 1.

An elongated window hole 12 is arranged on the front surface of the holder 1 and extends to the guide groove 2. The operating part 6 is movable is movable in the window hole 12 forward and backward. A back end of the window hole 12 has engaging recesses 13 at upper and lower edges of the window hole 12 respectively, and a front end of the window hole 12 has engaging recesses 14 at the upper and lower edges of the window hole 12 respectively. When the slider 3 is positioned at its backmost position, the engaging projections 11 engage with the engaging recesses 13 at the back end of the window hole 12, and when the slider 3 is positioned at its front end position, the engaging projections 11 engage with the engaging recesses 14 at the front side of the window hole 12.

The slider 3 is moved by urging the operating part 6 forward and backward after pushing a surface of the operating part 6 to release the engaging projections 11 from the engaging recesses 13 or 14.

A second embodiment of surgical knife is shown in FIGS. 6-9. Similarly to the first embodiment, the guide groove 2 is formed on the front surface of a holder 1, and the slider 3 is supported in the guide groove 2 to be movable forward and backward. Further, similarly to the first embodiment, the cutter blade 4 is connected to the slider 3 in such a manner that the cutter blade 4 projects from the front end of the holder 1 when the slider 2 is positioned at its front position, and the cutter blade 4 is completely contained in the holder 1 when the slider 2 is positioned at its backmost position.

The operating part 6 and the slider body 5 are separated from each other. The slider body 5 includes a transverse groove 17 in the vicinity of a central position of the slider body, and the elastic part 7 extends over the transverse groove 17 in a longitudinal direction of the slider body 5 as a cantilever. A core part of the operating part 6 fits in the transverse groove 17 in such a manner that the operating part 6 is movable transversely along the transverse groove 17. The operating part 6 has a downward extending engaging projection 19 for fixing the operating part 6. The elastic part 7 contacts an upper surface of the core part of the operating part 6 to urge elastically the operating part 6 downward.

The cutter blade 4, the slider body 5 and the operating part 6 fitting in the transverse groove 17 of the slider body 5 are received by the guide groove 2. When the slider 3 is positioned at its backmost position so that the cutter blade 4 is completely contained by the holder 1, the engaging projection 19 fits in an engaging hole 20 on a bottom surface of the guide groove 2 at a back side of the guide groove 2 so that the slider 3 is fixed. Since the operating part 6 is urged downward by the elastic part 7, this fixed condition of the slider 3 is stable.

When the slider 4 is positioned at its front end position so that the cutter blade 4 projects from the front end of the holder 1, the engaging projection 19 fits in an engaging hole 21 at a front side of the guide groove 2 so that the slider 3 is fixed. The slider 3 is moved by urging the operating part 6 forward and backward after pushing upward the surface of the operating part 6 to release the engaging projection 19 from the engaging hole 20 or 21.

Figure 14:
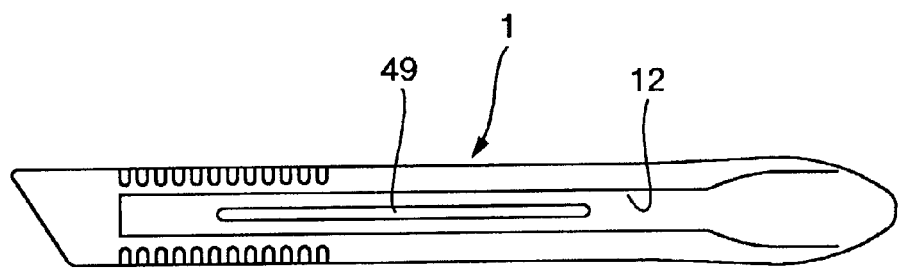
FIG. 14 is a front exploded view of the third embodiment.
Figure 14:
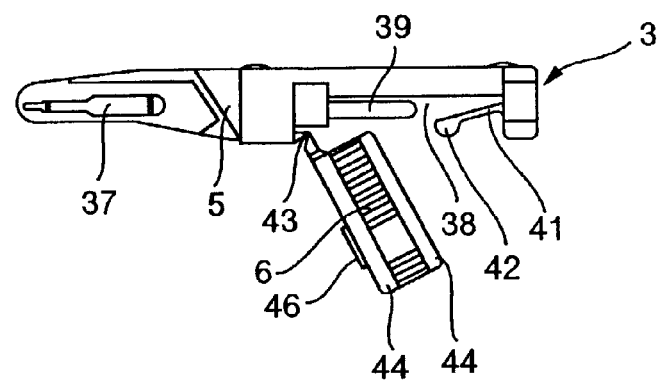
Figure 15:
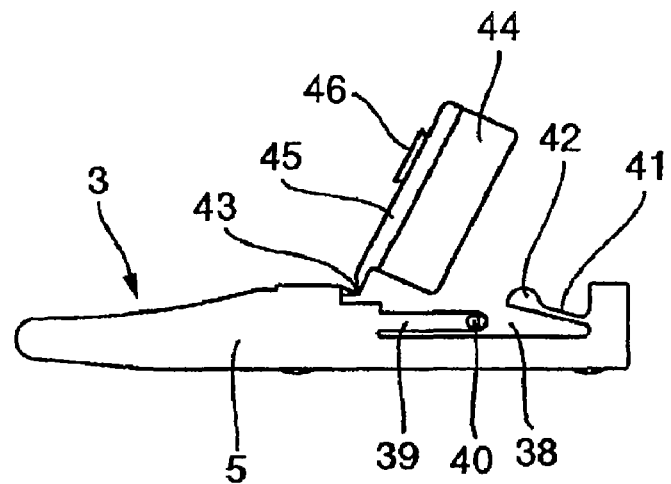
FIG. 15 is a back view of a slider of the third embodiment.

A third embodiment of surgical knife is shown in FIGS. 10-16. Reference numerals R and L indicate a radial direction and longitudinal direction of the window hole, respectively. As shown in FIGS. 14 and 15, the slider 3 is formed in one-piece by plastic injection molding. The slider 3 has the slider body 5 and the operating part 6. A cutter blade connecting protrusion 37 is arranged on a front end of the slider body 5, and a rectangular cut-off portion 38 is arranged at a side of the slider body 5 on a back half of the slider body 5. A guide piece 39 extends backward from a front side of an inner surface of the cut-off portion 38, and a terminating end of the guide piece 39 has a guide projection 40. An elastic piece 41 extends forward from a backside of the inner surface of the cut-off portion 38, and a terminating end of the guide piece 41 has a projection 42.

Figure 16:
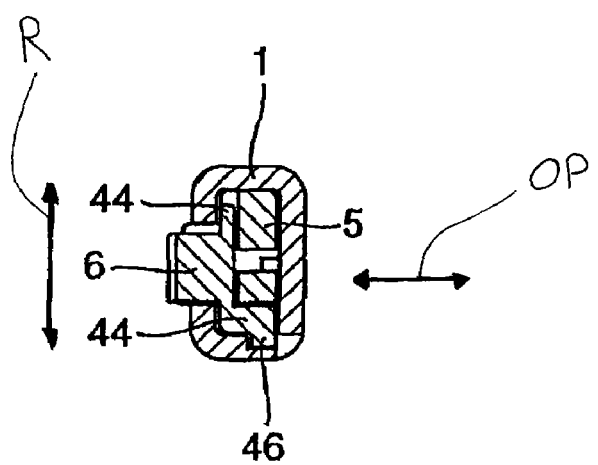
FIG. 16 is a cross sectional view of the third embodiment taken along an imaginary plane A-A in FIG. 11.

The operating part 6 is swingably connected through a hinge 43 to the slider body 5 in such a manner that the operating part can extend obliquely with respect to the slider body 5. As shown in FIG. 16, a width of the operating part 6 in the window hole 12 is narrower than a width of the window hole 12 so that the operating part 6 is movable in the window hole 12. A width of base portions 44 of the operating part 6 is wider than a width of the window hole 12 and the base portions 44 fit in the guide groove 2 so that the operating part 6 is prevented from slipping out of the window hole 12 to the near side. Reference numerals R and OP indicate a radial direction and opening direction of the window hole, respectively.

A side wall 45 extends integrally from a side edge of one of the base portions 44 in a direction perpendicular to the base portions 44. The hinge 43 is a thin portion of the side wall 45. The side wall 45 has an engaging protrusion 46 on an outer surface of the side wall 45, so that the engaging protrusion 46 engages with one of engaging recesses 47 and 48 to fix the slider 3.

When the engagement between the engaging protrusion 46 and the one of engaging recesses 47 and 48 is released and the slider 3 is moved in the guide groove 2, the operating part 6 is displaced upward by a distance corresponding to a protruding height of the engaging protrusion 46. By the upward displacement of the operating part 6, the side wall 45 contacts the projection 42 of the elastic piece 41, and by a reaction force against a deformation of the elastic piece 41, the operating part is urged in a counter direction. Whereby when the slider 3 is moved so that the engaging protrusion 46 reaches the engaging recess 47 or 48, the engaging protrusion 46 is securely fitted into the engaging recess 47 or 48 by a strong elastic force of the elastic piece 41.

The holder 1 of this embodiment has a guide hole 49 extending in a longitudinal direction of the guide groove 2 on a central position of a bottom surface of the guide groove 2. The guide hole 49 receives the guide projection 40 of slider 3 so that the slider 3 slides smoothly. When the slider 3 is fixed in the guide groove 2, that is, the engaging protrusion 46 fits in the engaging recess 47 or 48, the guide projection 40 is positioned at one of ends of the guide hole 49. Therefore, the slider 3 can be stopped to securely fit the engaging protrusion 46 in the engaging recess 47 or 48, even when the slider 3 is moved in a high speed. Although a back end of the holder 1 is opened in such a manner that the slider 3 is removed from the holder 1 through the back end thereof, the movement of the guide projection 40 is limited by a back end of the guide hole 49 so that the slider 3 is prevented from being removed from the holder 1 through the back end thereof.

A fourth embodiment of surgical knife as shown in FIGS. 17-22 corresponds to the claimed inventions as recited in claims 14-17. Similarly to the above embodiments, the guide groove 2 is formed on the front surface of a holder 1, and the slider 3 is supported in the guide groove 2 to be movable forward and backward. Further, similarly to the above embodiments, the cutter blade 4 is connected to the slider 3 in such a manner that the cutter blade 4 projects from the front end of the holder 1 when the slider 2 is positioned at its front position, and the cutter blade 4 is completely contained in the holder 1 when the slider 2 is positioned at its backmost position.

The operating part 6 of a slightly elongated plate shape has a pair of pin supporting pieces 22 on a base end thereof. The pin supporting pieces 22 have respective pin holes 23. The operating part 6 has projections 24 on respective upper and lower surfaces of the operating part 6 to fix the slider.

The slider body 5 has a pin-receiving hole 25 on a surface thereof. The operating part 6 is swingably supported by the slider body 5 by arranging the pin receiving hole 25 between the pin supporting pieces 22, and inserting a pin 26 through the pin holes 23 and the pin receiving hole 25 with fixing the pin 26.

Figure 20:
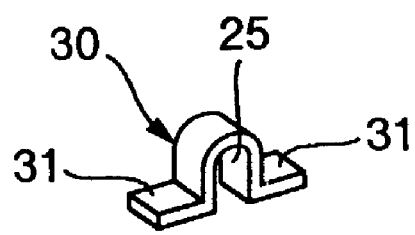
FIG. 20 is a schematic oblique projection view showing a connecting structure among an operating part, a holder body and so forth in the fourth embodiment.
Figure 20:
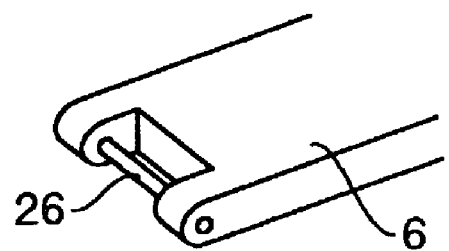
Figure 20:
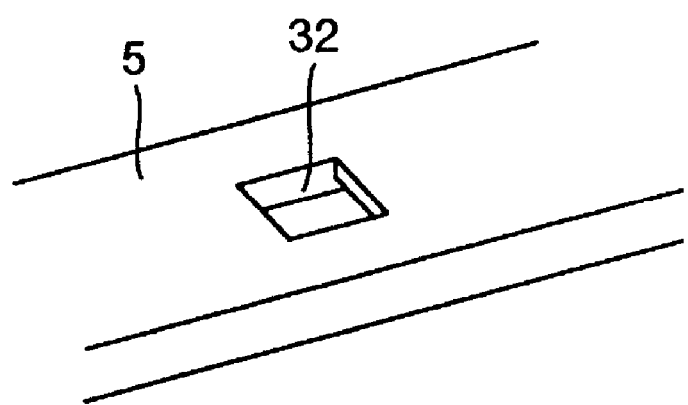
Figure 20:
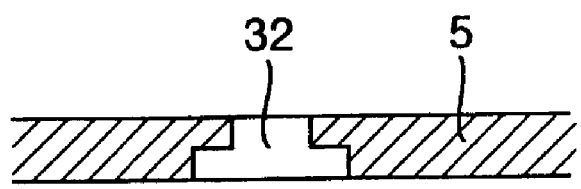

As shown in FIG. 20, the pin receiving hole 25 is formed by that base plates 31 of a pin receiving piece 30 forming the pin receiving hole 25 are inserted into an enlarged portion of a stepwise rectangular hole 32 of the slider body 5 in such a manner that a U-shaped portion of the pin receiving piece 30 extends through the rectangular hole 32 to project from a surface of the slider body 5.

Figure 17:
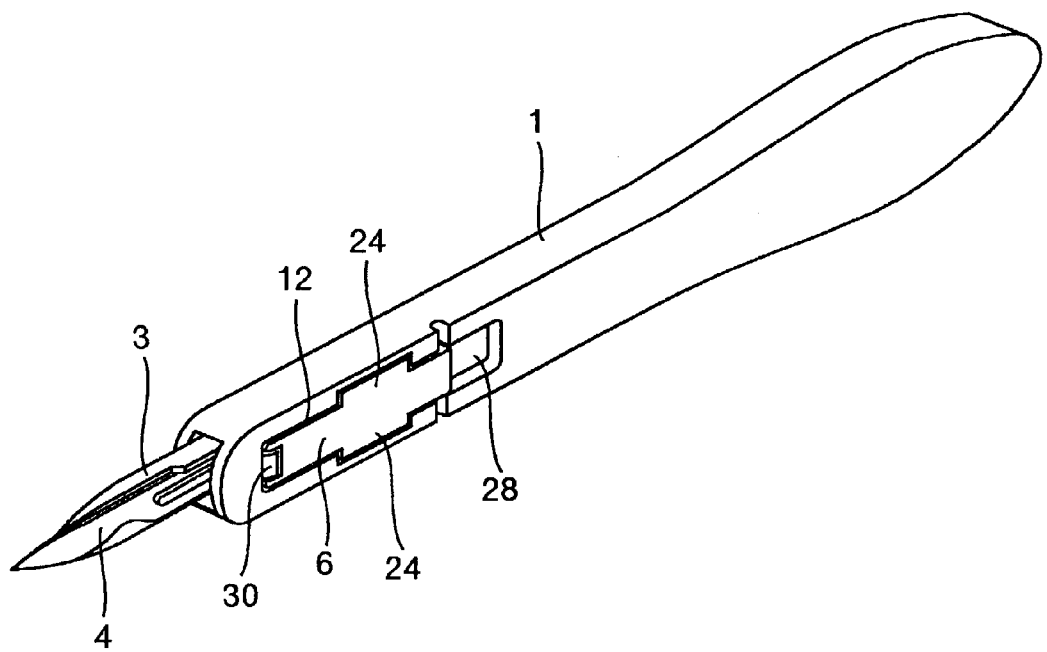
FIG. 17 is a schematic oblique projection view showing a surgical knife of a fourth embodiment of the invention with a cutter blade positioned at its projected position.
Figure 18:
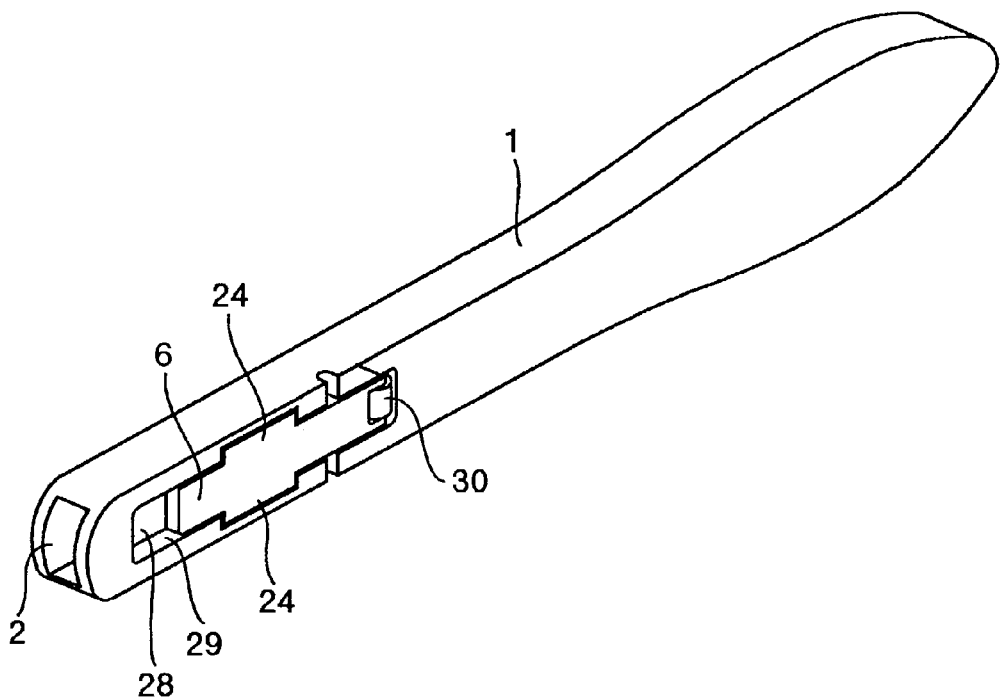
FIG. 18 is a schematic oblique projection view showing the surgical knife of the fourth embodiment with the cutter blade positioned at its withdrawn position.
Figure 19:
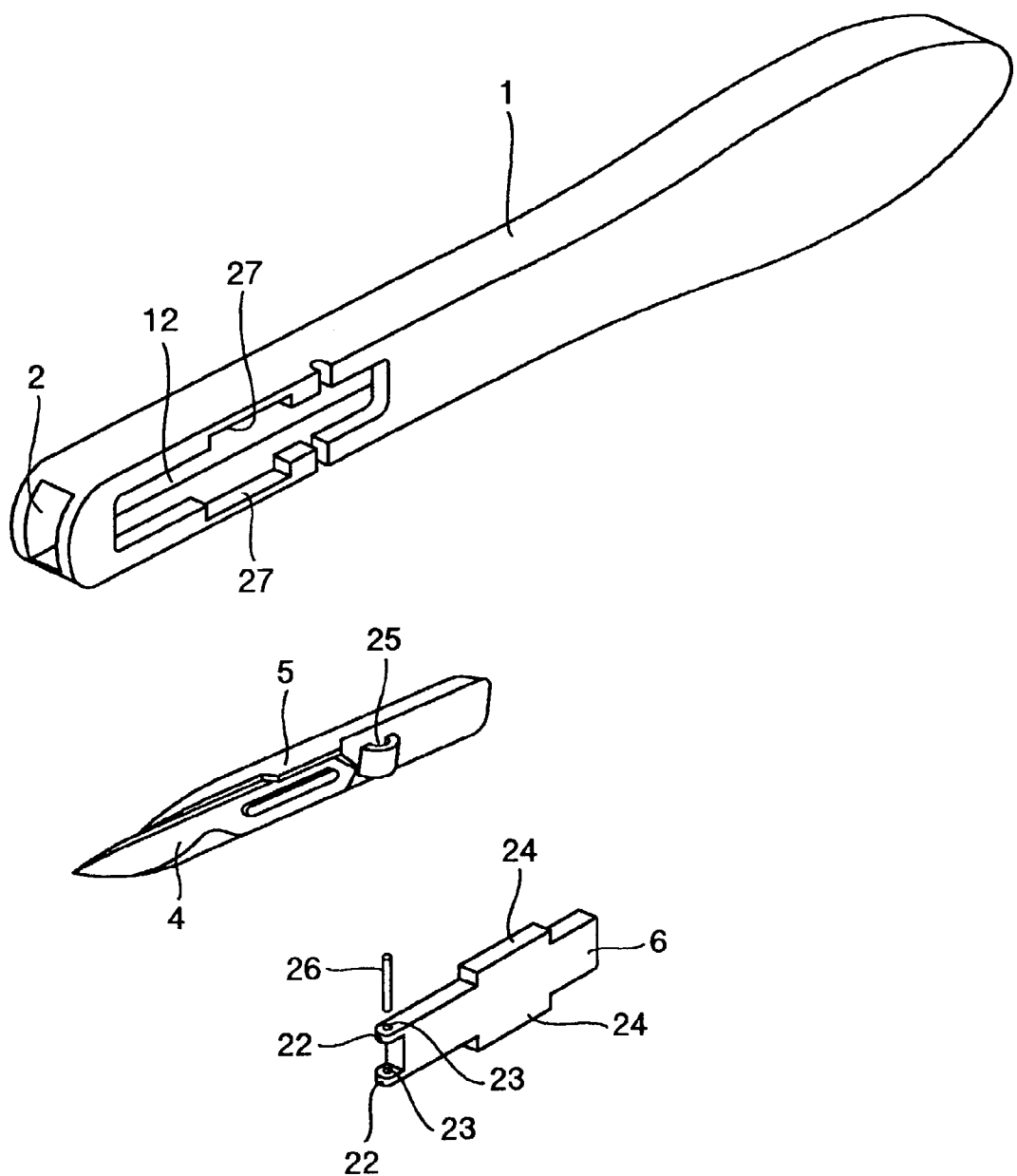
FIG. 19 is a schematic oblique projection exploded view of the surgical knife of the fourth embodiment.
Figure 21:
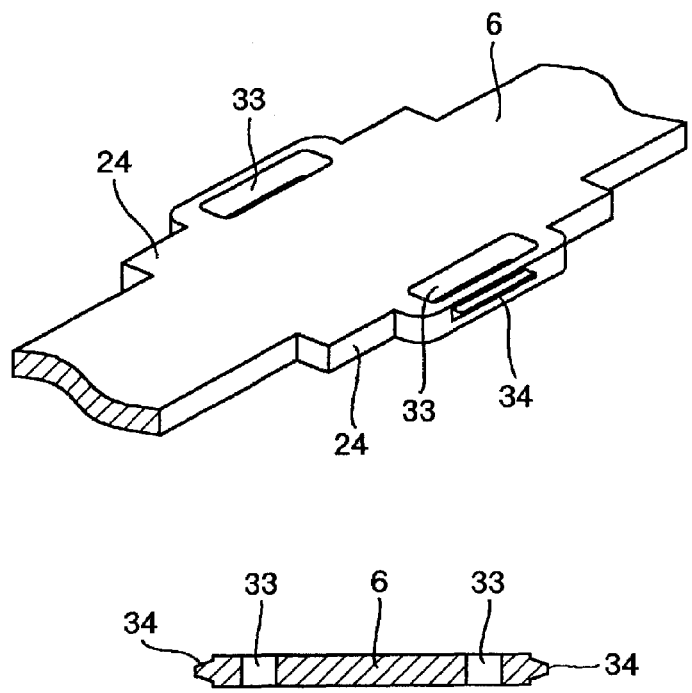
FIG. 21 is a combination of an oblique projection view and a cross sectional view showing a projecting portion of the operating part of the fourth embodiment.

Recesses 27 for receiving therein the projections 24 are formed on respective upper and lower edges of the window hole 12 of the holder 1. When the cutter blade 4 is projected from the front end of the holder 1, as shown in FIG. 17, the base end of the operating part 6 is positioned at the front end of the window hole 12 and is fitted in the window hole 12. At this time, since the projections 24 are fitted in the recesses 27 respectively, the slider 3 is prevented from moving forward and backward. A space 28 is used to facilitate pulling up the operating part 6 when the operating part 6 is reversed. As shown in FIG. 21, each of the projections 24 may have an engaging protrusion 34 extending over a slit 33 at an outside of the projection 24, and each of the recesses 27 may have an engaging recess (not shown) for engaging with the engaging protrusion 34 on an inner surface of the recess 27, so that an engagement between the engaging protrusion 34 and the engaging recess prevents securely the operating part 6 from moving out of the window hole 12.

If a thickness of the operating part 6 is substantially equal to a thickness of a window hole peripheral area 29 of the guide groove 2 as recited in claim 17, the operating part 6 is prevented from protruding from the surface of the holder 1, so that the slider 3 is securely prevented from being moved undesirably.

When the cutter blade 4 is completely contained by the holder 1, the operating part 6 is pulled up to release the engagement between the recesses 27 and the projections 24 in a condition shown in FIG. 17, subsequently the operating part 6 is moved to position the base end of the operating part 6 at the backmost position of the window hole 12, and finally the operating part 6 is fitted into the window hole 12 to insert the projections 24 into the recesses 27.

Figure 22:
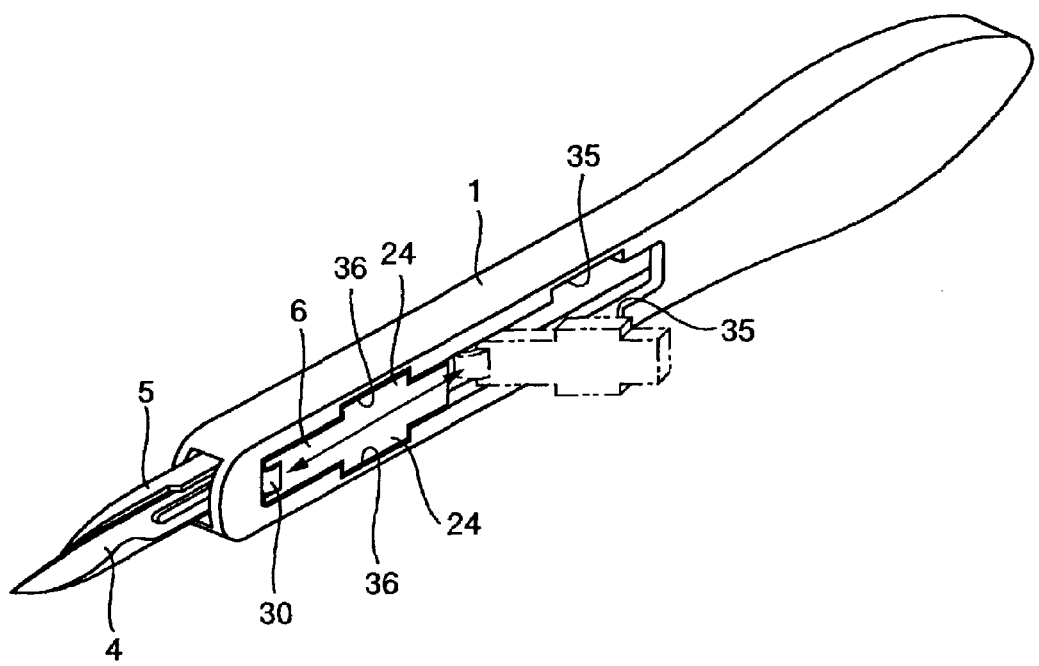
FIG. 22 is a schematic oblique projection view showing a surgical knife of a fifth embodiment of the invention with a cutter blade positioned at its projected position.

FIG. 22 shows a fixing method of the slider 3 as recited in claim 16 as a fifth embodiment. The cutter blade 4, the slider body 5, the operating part 6 and a swing mechanism between the slider body 5 and the operating part 6 of this embodiment are the same as those of the fourth embodiments.

The window hole 12 of this embodiment is longer than that of the fourth embodiment, a pair of recesses 35 at a back side of the window hole 12 and a pair of recesses 36 at a front side of the window hole 12 correspond to the recesses 27 of the fourth embodiment. When the cutter blade 4 is projected from the front end of the holder 1, the projections 24 are fitted in the recesses 36 at the front side of the window hole 12. When the cutter blade 4 is contained in the holder 1, the projections 24 are fitted in the recesses 35 at the backside of the window hole 12.

What is claimed is:
1. A surgical knife comprising,
a cutter blade including at least one sharp edge and lateral surfaces opposed to each other, between which lateral surfaces the at least one sharp edge is arranged as seen in a direction perpendicular to a thickness direction of the cutter blade, a holder including a longitudinal hole extending in a longitudinal direction of the holder and containing at least a part of the cutter blade, and a guide groove extending in the longitudinal direction and in a thickness direction of the holder to extend from the longitudinal hole and open to a front surface of the holder extending in a front surface direction parallel to the lateral surfaces of the cutter blade, and a slider connected to the cutter blade and movable along the guide groove between a front position for making the cutter blade project from a front end of the holder and a back position for making the cutter blade be contained in the holder, wherein the slider has a slider body holding thereon the cutter blade and being supported in the longitudinal hole, and an operating part swingably coupled to the slider body to be movable with respect to the holder so that a first portion of the operating part in the longitudinal hole is disengaged from the holder to release the slider from the holder and engaged with the holder to fix the slider to the holder at each of the front and back positions, and the operating part has a second portion protruding in the thickness direction from the first portion of the operating part in the longitudinal hole through the guide groove to project from the front surface in the thickness direction and being movable in a radial direction in a plane of the guide groove as seen in the thickness direction, and wherein the slider has an elastic member arranged between the operating part and the slider body to elastically urge the first portion of the operating part against the holder, and has a hinge arranged separately from the elastic member between the slider body and the operating part to swingably couple the operating part to the slider body.

* * * * *